(12) United States Patent
Gobbi et al.

(10) Patent No.: US 10,004,817 B2
(45) Date of Patent: Jun. 26, 2018

(54) DIAZACARBAZOLE DERIVATIVES AS TAU-PET-LIGANDS

(71) Applicant: Hoffmann-La Roche Inc., Little Falls, NJ (US)

(72) Inventors: Luca Gobbi, Buus (CH); Henner Knust, Rheinfelden (DE); Matthias Koerner, Grenzach-Wyhlen (DE); Dieter Muri, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 95 days.

(21) Appl. No.: 15/093,366

(22) Filed: Apr. 7, 2016

(65) Prior Publication Data

US 2016/0220712 A1    Aug. 4, 2016

Related U.S. Application Data

(63) Continuation of application No. PCT/EP2014/071283, filed on Oct. 6, 2014.

(30) Foreign Application Priority Data

Oct. 8, 2013  (EP) .................................... 13187764

(51) Int. Cl.
*A61K 51/00* (2006.01)
*A61M 36/14* (2006.01)
*A61K 51/04* (2006.01)
*C07D 471/04* (2006.01)
*C07D 471/14* (2006.01)

(52) U.S. Cl.
CPC ........ *A61K 51/0455* (2013.01); *C07D 471/04* (2013.01); *C07D 471/14* (2013.01)

(58) Field of Classification Search
CPC .. A61K 51/00; A61K 51/0455; C07D 471/04; C07D 471/14; C07D 211/06; C07D 295/00; C07D 213/02; C07D 207/00; C07D 207/18; C07D 207/30; C07D 209/40; C07D 209/04; C07D 209/44
USPC .... 424/1.11, 1.65, 1.81, 1.85, 1.89, 9.1, 9.2, 424/9.3, 9.4, 9.5, 9.6; 546/184, 255; 548/400, 469, 470, 565, 560
See application file for complete search history.

(56) References Cited

U.S. PATENT DOCUMENTS

2010/0239496 A1   9/2010  Gangadharmath et al.
2015/0368244 A1*  12/2015 Dyke .................. C07D 471/14
                                                    514/252.16

OTHER PUBLICATIONS

International Preliminary Report on Patentability for International Patent Application No. PCT/EP2014/071283.

* cited by examiner

*Primary Examiner* — D L Jones
(74) *Attorney, Agent, or Firm* — Tamara A. Kale (57) ABSTRACT

The present invention relates to compounds that may be used for binding and imaging tau aggregates and related beta-sheet aggregates including, besides others, beta-amyloid aggregates or alpha-synuclein aggregates.

6 Claims, 1 Drawing Sheet

DIAZACARBAZOLE DERIVATIVES AS TAU-PET-LIGANDS

This application is a continuation of International Application No. PCT/EP2014/071283, filed Oct. 6, 2014, which claims priority to EP Appl. No. 13187764.9, filed Oct. 8, 2013, each of which is incorporated herein by reference in its entirety.

The present invention relates to a compound of general formula wherein
R is hydrogen or tritium; and
F is fluoro or $^{18}$fluoro;
or to a pharmaceutically acceptable acid addition salt.

Compounds of formula I include 2-(6-fluoro-pyridin-3-yl)-9H-dipyrido[2,3-b;3',4'-d]pyrrole, $^3$H-2-(6-fluoro-pyridin-3-yl)-9H-dipyrido[2,3-b;3',4'-d]pyrrole and [18F]-2-(6-fluoro-pyridin-3-yl)-9H-dipyrido[2,3-b;3',4'-d]pyrrole.

Compounds with similar generic basic structure are described in WO2009/102498 for in vivo imaging of amyloid deposits for diagnosing Alzheimer's disease. No tricyclic compounds with 3 N atoms are described specifically.

It has been shown that the present compounds may be used for binding and imaging tau aggregates and related beta-sheet aggregates including besides others beta-amyloid aggregates or alpha-synuclein aggregates, especially for use in binding and imaging tau aggregates in Alzheimer patients.

Alzheimer's disease (AD) is a progressive neurodegenerative disorder characterized by cognitive decline, irreversible memory loss, disorientation and language impairment (Arch. Neurol. 1985, 42(11), 1097-1105). Postmortem examination of AD brain sections reveals abundant senile plaques (SPs), composed of beta amyloid (Aβ) peptides, and numerous neurofibrillary tangles (NFTs) formed by filaments of hyperphosphorylated tau protein.

Tau belongs to the family of microtubule-associated proteins and is mainly expressed in neurons where it plays an important role in the assembly of tubulin monomers into microtubules to constitute the neuronal microtubule network as tracks for axonal transport (Brain Res. Rev. 2000, 33(1), 95-130). Tau is translated from a single gene located on chromosome 17 and the expression is developmentally regulated by an alternative splicing mechanism generating six different isoforms in the human adult brain that can be distinguished by their number of binding domains. The underlying mechanisms leading to tau hyperphosphorylation, misfolding and aggregation are not well understood, but the deposition of tau aggregates follows a stereotyped spatiotemporal pathway both at the intracellular levels as well as on the level of brain topography.

The recent discovery of tau gene mutations leading to frontotemporal dementia (FTD) with parkinsonism linked to chromosome 17 has reinforced the predominant role attributed to tau in the pathogenesis of neurodegenerative disorders and underlined the fact that distinct sets of tau isoforms expressed in different neuronal populations could lead to different pathologies (Biochim. Biophys. Acta 2005, 1739 (2) 240-250). Neurodegenerative diseases characterized by pathological tau accumulation are termed 'tauopathies' (Ann. Rev. Neurosci. 2001, 24, 1121-1159). Besides AD and FTD, other tauopathies include progressive supranuclear palsy (PSP), tangle-predominant dementia, Pick's disease, frontotemporal lobar degeneration (FTLD), Down's syndrome and others.

A direct correlation has been established between the progressive involvement of neocortical areas and the increasing severity of dementia, suggesting that pathological tau aggregates such as NFTs are a reliable marker of the neurodegenerative process. The degree of NFT involvement in AD is defined by Braak stages (Acta Neuropathol. 1991, 82, 239-259). Braak stages I and II are defined when NFT involvement is confined mainly to the transentorhinal region of the brain, stages III and IV are diagnosed when limbic regions such as the hippocampus are involved, and stages V and VI when extensive neocortical involvement is found.

Presently, detection of tau aggregates is only possible by histological analysis of biopsy or autopsy materials. In vivo imaging of tau pathology would provide novel insights into deposition of tau aggregates in the human brain and allow to non-invasively examine the degree of tau pathology, quantify changes in tau deposition over time, assess its correlation with cognition and analyze the efficacy of an anti-tau therapy. Potential ligands for detecting tau aggregates in the living brain must cross the blood-brain barrier and possess high affinity and specificity for tau aggregates. To this end, successful neuroimaging radiotracers must have appropriate lipophilicity (logD 1-3) and low molecular weight (<450), show rapid clearance from blood and low non-specific binding.

The object of the present application is to find an imaging tool which will improve diagnosis by identifying potential patients with excess of tau aggregates in the brain, which may be likely to develop Alzheimer's disease. It will also be useful to monitor the progression of the disease. When an anti-tau aggregate drug becomes available, imaging tau tangles in the brain may provide an essential tool for monitoring treatment.

A further object of the present invention is a method of imaging tau-aggregate deposits, comprising
 introducing into a mammal a detectable quantity of a composition
 allowing sufficient time for the compound of formula I to be associated with tau-aggregate deposits, and
 detecting the compound associated with one or more tau-aggregate deposits.

A further object of the present invention is a pharmaceutical composition, containing compounds of formula I and pharmaceutically acceptable carriers, which may be used for identifying potential patients.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-7 carbon atoms. Examples for "alkyl" are methyl, ethyl, n-propyl, and isopropyl.

$^3$H denotes a tritium atom.

F denotes a fluoro atom or a $^{18}$fluoro atom.

The term "leaving group" denotes halogen or sulfonate. Examples of sulfonate are tosylate, mesylate, triflate, nosylate or brosylate.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

It has been found that the compounds of formula I may be used for binding and imaging tau aggregates and related beta-sheet aggregates including besides others beta-amyloid aggregates or alpha-synuclein aggregates.

One embodiment of the present invention are compounds of formula I which compounds are 2-(6-fluoro-pyridin-3-yl)-9H-dipyrido[2,3-b;3',4'-d]pyrrole, $^3$H-2-(6-fluoro-pyridin-3-yl)-9H-dipyrido[2,3-b;3',4'-d]pyrrole and [18F]-2-(6-Fluoro-pyridin-3-yl)-9H-dipyrido[2,3-b;3',4'-d]pyrrole One embodiment of the present invention are further compounds of formula I wherein R is hydrogen, which compound is 2-(6-fluoro-pyridin-3-yl)-9H-dipyrido[2,3-b;3',4'-d]pyrrole.

One embodiment of the present invention are further compounds of formula I wherein R is tritium, for example the following compound $^3$H-2-(6-fluoro-pyridin-3-yl)-9H-dipyrido[2,3-b;3',4'-d]pyrrole.

One embodiment of the invention are further compounds of formula I, wherein F is $^{18}$fluoro, for example [18F]-2-(6-fluoro-pyridin-3-yl)-9H-dipyrido[2,3-b;3',4'-d]pyrrole The position for R in formula I, if R is tritium, is the most likely ones. But tritium may also be found in small amounts in other positions of the molecule. Normally, only one of R is tritium.

The compounds of formula I may be used in binding and imaging tau aggregates, beta-amyloid aggregates, alpha-synuclein aggregates or huntingtin aggregates.

The preferred use of compounds of formula I is the use in binding and imaging tau aggregates in Alzheimer patients.

Furthermore, the compounds of formula I may be used in a tau-binding study.

The compounds of formula I are suitable for diagnostic imaging of tau-aggregates in the brain of a mammal.

The invention is also used for diagnostic imaging of tau-aggregate deposits in the brain of a mammal.

The present compounds of formula I

I and their pharmaceutically acceptable salts can be prepared by processes described below, which process comprises a) coupling a compound of formula 2 (X=Cl, Br)

2 with suitable boronic acids or boronic acid esters of formula 3

3 wherein R' is hydrogen or lower alkyl, to afford compounds of formula I

I wherein R is hydrogen, and, if desired, converting the obtained compound into pharmaceutically acceptable acid addition salts or into compounds of formula I, wherein R is tritium;

or b) coupling compounds of formula 4

4

(X = Br, Cl, NO$_2$)

with suitable fluorinating reagents selected from potassium fluoride or tetrabutylammonium fluoride, to afford compounds of formula I wherein the substituent R is hydrogen and, if desired, converting the compound obtained into pharmaceutically acceptable acid addition salts or into compounds of formula I, wherein R is tritium c) reacting a compound of formula I wherein R is hydrogen, with tritium gas in the presence of a catalyst, e.g. iridium, ruthenium, rhodium or palladium containing complexes in a suitable solvent, e.g. dichloromethane, chlorobenzene, DMF, DMSO or mixtures thereof to afford compound of formula I wherein R is tritium, and, if desired, converting the compounds obtained into pharmaceutically acceptable acid addition salts, or d) dissolving a compound of formula in dimethylsulfoxide and sonicate prior to end of bombardment with aqueous [18]fluoride ion to a compound of formula and, if desired, converting the compounds obtained into pharmaceutically acceptable acid addition salts.

The following schemes 1-2 describe the processes for the preparation of compounds of formula I in more detail. The starting materials are known compounds or may be prepared according to methods known in the art.

The preparation of compounds of formula I of the present invention may be carried out in sequential or convergent synthetic routes. The skills required for carrying out the reactions and purifications of the resulting products are known to those skilled in the art. The sub stituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1-2, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

According to scheme 1, compounds of formula I, wherein R is hydrogen, can be prepared starting from protected 4-amino-pyridines 5 (X=Cl, Br) and 2,6-di-halogenated pyridine boronic acids 6 (R'=H, lower alkyl). Transition-metal catalyzed cross-coupling conditions using a catalyst system like e.g. Pd(OAc)$_2$ and PPh$_3$ and a base like e.g. triethylamine in a suitable solvent like DMF results in bipyridines 7. Deprotection and intramolecular cyclisation can be performed as one-pot procedure using a base like e.g. potassium carbonate and an activator like e.g. 18-crown-6 in a suitable solvent like DMF and affords 1,6-diazacarbazole intermediate 2. Final transformation into compounds of formula I can be accomplished by a direct transition-metal catalyzed cross-coupling reaction using appropriate pyridine boronic acids 3, a catalyst like e.g. Pd(dppf)Cl$_2$ and a base like e.g. potassium carbonate in a suitable solvent like DMF. Alternatively, 1,6-diazacarbazole 2 is first converted into protected intermediates 8 via reaction with a suitable reagent, e.g. di-tert-butyldicarbonate, in a suitable solvent like e.g. DMF, followed by transition-metal catalyzed cross-coupling reaction towards intermediates 9 using appropriate pyridine boronic acids 3, a catalyst like e.g. Pd(dppf)Cl$_2$ and a base like e.g. potassium carbonate in a solvent like DMF. Deprotection is then leading to compounds of formula I.

Scheme 2

According to scheme 2, a compound of formula I, wherein R is hydrogen, can be prepared by treating a compound of formula 4 (X=Br, Cl, nitro); prepared according to the synthesis of compounds of formula I described in scheme 1, with a suitable fluorinating reagent like e.g. potassium fluoride or tetrabutylammonium fluoride in a suitable solvent like e.g. DMF or DMSO.

Compounds of formula I with R being tritium or F being $^{18}$F may be prepared in conventional manner as described in the specific examples. Compounds of formula I do not contain simultaneously tritium and $^{18}$F.

Isolation and Purification of the Compounds

Isolation and purification of the compounds and intermediates described herein can be performed, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be found by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be precipitated by addition of a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds were investigated in accordance with the test given hereinafter.

TAU Radioligand-In-Vitro Displacement Assay

Figure 2:
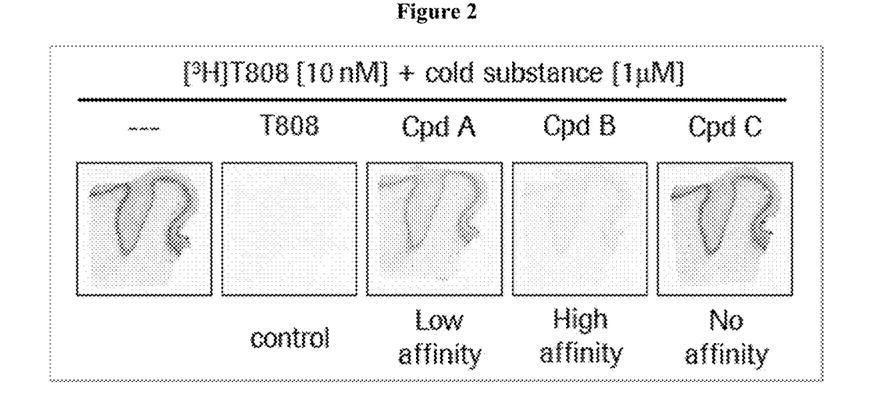
FIG. 2: Tau radioligand in-vitro displacement assay results using human Alzheimer's disease brain sections.

This in vitro binding assay assesses the affinity of compounds for native tau aggregates. The compounds are co-incubated with the well-established tau specific radioligand [$^3$H]T808 and the compound's displacement potency of [$^3$H]T808 binding is determined by in vitro autoradiography using human Alzheimer's disease (AD) brain sections (see FIG. 2).

Materials

AD human brains are purchased from Banner Sun Health Research Institute (Sun City, Ariz., U.S.A.). Pathological diagnosis of AD is made according to standard NIA-Reagan Institute criteria based on neuropathological data. The radioligand [$^3$H]T808 was synthesized in-house ([$^3$H]-2-[4-(2-Fluoro-ethyl)-piperidin-1-yl]-benzo[4,5]imidazo[1,2-a]pyrimidine, radiochemical purity 99.0%). As a reference cold T808 is used (2-[4-(2-Fluoro-ethyl)-piperidin-1-yl]-benzo[4,5]imidazo[1,2-a]pyrimidine). For the autoradiography FujiFilm Imaging Plates (BAS-IP TR 2025) are exposed to the sections and read with a FujiFilm IP reader (BAS-5000).

Method

Ten μm thick human AD brain sections are generated with a cryostat (Leica CM3050) at −17° C. chamber temperature and −15° C. object temperature. Sections are transferred to Histobond+ microscope slides (Marienfeld Laboratory Glassware). After drying for 3 hours at room temperature the sections are stored at −20° C. The sections are incubated with the radioligand (10 nM) and the respective cold compound (at various concentrations) in 50 mM Tris buffer, pH 7.4 at room temperature for 30 min. After washing 3×10 min at 4° C. in 50 mM Tris buffer, pH 7.4 and 3 quick dips in $H_2O$ dist. at 4° C. the sections are dried at 4° C. for 3 h. The sections are placed in a FujiFilm Cassette (BAS 2025), exposed with an Imaging Plate for five days and afterwards scanned with a resolution of 25 μM per pixel.

Data Analysis

Figure 1:
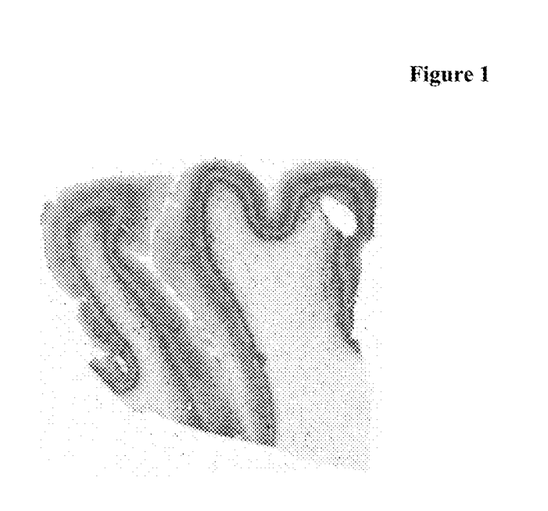
FIG. 1: Autoradiogram of $^3$H-2-(6-fluoro-pyridin-3-yl)-9H-dipyrido[2,3-b;3',4'-d]pyrrole.

The signal intensity (Dens-PSL/mm2) in the region of interest (ROI) of the autoradiogram is quantified with the software MCID analysis (version 7.0, Imaging Research Inc.). The specific binding (SB) of [$^3$H]T808 binding in absence or in presence of a compound is calculated by subtracting the non-specific binding signal in the white matter, thus yielding $SB_{[3H]T808\ only}$ and $SB_{compund}$. The % displacement by the various compounds is calculated as following:

% displacement=100−($SB_{compund}/SB_{[3H]T808\ only}$)*100.

Validation Data

In each experiment cold T808 is used as a positive internal control. Co-incubation of equimolar amounts of hot and cold T808 is expected to reduce specific binding by approximately 50%.

REFERENCES

A. K. Szardenings et al. 'Imaging agents for detecting neurological disorders'. US Patent Application US20110182812

W. Zhang et al., 'A highly selective and specific PET tracer for imaging of tau pathologies'. *Journal of Alzheimer's Disease* 31 (2012) 601-612.

TABLE 1

| Structure | Name | % displacement of [$^3$H]T808 (10 nM) | Expl. |
|---|---|---|---|
|  | 2-(6-fluoro-pyridin-3-yl)-9H-dipyrido[2,3-b;3',4'-d]pyrrole | 43 | 1 |

TABLE 1-continued

| Structure | Name | % displacement of [³H]T808 (10 nM) | Expl. |
|---|---|---|---|
| | ³H-2-(6-fluoro-pyridin-3-yl)-9H-dipyrido[2,3-b;3',4'-d]pyrrole | | 2 |
| | [18F]-2-(6-fluoro-pyridin-3-yl)-9H-dipyrido[2,3-b;3',4'-d]pyrrole | | 3 |

Figure 1:

Autoradiogram of ³H-2-(6-fluoro-pyridin-3-yl)-9H-dipyrido[2,3-b;3',4'-d]pyrrole incubated with a human cortical brain section obtained from a Braak V staged AD patient. The radioligand concentration was 3.2 nM. The radioligand shows a punctate staining of tau aggregates in a layered distribution pattern.

The compounds of formula I and pharmaceutically acceptable salts thereof can be used in the form of pharmaceutical preparations. The pharmaceutical preparations can be administered in form of injection solutions.

The compounds of formula I and pharmaceutically acceptable salts thereof can be processed with pharmaceutically inert, inorganic or organic carriers for the production of pharmaceutical preparations. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case.

EXPERIMENTAL SECTION

Example 1

2-(6-Fluoro-pyridin-3-yl)-9H-dipyrido[2,3-b;3',4'-d]pyrrole

Step 1: tert-Butyl N-[3-(2,6-dichloro-3-pyridyl)-4-pyridyl]carbamate

A pre-heated flask was evacuated and back-filled with argon several times and charged with tert-butyl 3-iodopyridin-4-ylcarbamate (4.56 g, 14.2 mmol), 2,6-dichloropyridin-3-ylboronic acid (5.46 g, 28.4 mmol), Pd(OAc)₂ (320 mg, 1.42 mmol) and triphenylphosphine (371 mg, 1.41 mmol) under argon atmosphere. Triethylamine (4.32 g, 5.94 mL, 42.7 mmol) in DMF (137 mL) was added and the reaction mixture was heated to 100° C. and stirred for 3 h. The solvent was evaporated almost completely. Water was added and the crude product suspension was extracted with ethyl acetate twice. The combined organic layer was washed with water (3×), dried over Na₂SO₄, filtered and the solvent was evaporated. Trituration of the crude product with dichloromethane afforded 1.92 g of the desired product. The dichloromethane phase was evaporated and purified by flash chromatography (using silica gel and an ethyl acetate/heptane gradient) to yield in total 3.39 g (~90% purity, 63% yield) of tert-butyl N-[3-(2,6-dichloro-3-pyridyl)-4-pyridyl]carbamate as light yellow solid.

MS: m/z=340.1 (M+H)⁺.

Step 2: 2-Chloro-9H-dipyrido[2,3-b;3',4'-d]pyrrole

A suspension of tert-butyl N-[3-(2,6-dichloro-3-pyridyl)-4-pyridyl]carbamate (264 mg, 776 µmol), potassium carbonate (215 mg, 1.55 mmol) and 18-crown-6 (226 mg, 854 µmol) in DMF (15.8 mL) was heated to 100° C. and stirred for 3 h under an atmosphere of argon. Water was added and the crude product suspension was extracted with ethyl acetate twice. The combined organic layer was washed with water (twice), brine, dried over Na₂SO₄, filtered and the solvent was evaporated. Trituration of the crude product with little methanol afforded 2-chloro-9H-dipyrido[2,3-b;3',4'-d]pyrrole (105 mg, 63% yield) as light yellow solid.

MS: m/z=204.3 (M+H)⁺.

Step 3: 2-Chloro-dipyrido[2,3-b;3',4'-d]pyrrole-9-carboxylic acid tert-butyl ester A suspension of sodium hydride (26.5 mg, 607 µmol) in dry DMF (1.5 mL) was cooled to 0° C. and under argon a solution of 2-chloro-9H-dipyrido[2,3-b;3',4'-d]pyrrole (103 mg, 506 µmol) in dry DMF (3.0 mL) was added. Stirring was continued at 0° C. for 10 min and at r.t. for 30 min. After cooling down to 0° C. and addition of di-tert-butyl dicarbonate (132 mg, 141 µL) in dry DMF (0.75 mL) was added and stirring was continued at r.t. overnight. Water was added and the reaction mixture was extracted twice with ethyl acetate. The combined organic layer was washed with water (twice) and brine, dried over $Na_2SO_4$, filtered and evaporated. 2-Chloro-dipyrido[2,3-b;3',4'-d]pyrrole-9-carboxylic acid tert-butyl ester was obtained after purification by flash chromatography (using silica gel and a methanol/dichloromethane gradient) as off-white solid (113 mg, 73.5%).

MS: m/z=304.1 $(M+H)^+$.

Step 4: 2-(6-Fluoro-pyridin-3-yl)-dipyrido[2,3-b;3',4'-d]pyrrole-9-carboxylic acid tert-butyl ester A microwave vessel was charged under argon atmosphere with 2-chloro-dipyrido[2,3-b;3',4'-d]pyrrole-9-carboxylic acid tert-butyl ester (100 mg, 329 µmol), 2-fluoro-5-(4,4,5,5-tetramethyl-1,3,2-dioxaborolan-2-yl)pyridine (147 mg, 658 µmol), potassium carbonate (137 mg, 988 µmol) and 1,1'-bis(diphenylphosphino)ferrocene-palladium(II)dichloride dichloromethane complex (10.8 mg, 13.2 µmol) and the vessel was sealed, evacuated and back-filled with argon. DMF (7 mL) was added and the reaction mixture was heated to 90° C. and stirred for 17 h. The reaction mixture was filtered. Water was added to the filtrate and the reaction mixture was extracted twice with ethyl acetate. The combined organic layer was washed with water (3×), dried over $Na_2SO_4$, filtered and evaporated. Trituration of the crude product mixture with little methanol afforded 2-(6-fluoro-pyridin-3-yl)-9H-dipyrido[2,3-b;3',4'-d]pyrrole (m/z=265.1 $(M+H)^+$) as light red solid (23 mg with 80% purity, 21%). The liquid was evaporated and purified by flash chromatography (using silica gel and a methanol/dichloromethane gradient) to afford 2-(6-fluoro-pyridin-3-yl)-dipyrido[2,3-b;3',4'-d]pyrrole-9-carboxylic acid tert-butyl ester as off-white solid (12 mg, 10%).

MS: m/z=365.2 $(M+H)^+$.

Step 5: 2-(6-Fluoro-pyridin-3-yl)-9H-dipyrido[2,3-b;3',4'-d]pyrrole

A light yellow solution of 2-(6-fluoro-pyridin-3-yl)-dipyrido[2,3-b;3',4'-d]pyrrole-9-carboxylic acid tert-butyl ester (22 mg, 60.4 µmol) and trifluoroacetic acid (33.3 µL, 432 µmol) in dichloromethane (0.5 mL) was stirred at r.t. overnight. After cooling to 0° C. triethylamine (70 µL, 503 µmol) was added and all volatiles were removed. The crude material was purified by preparative HPLC (using a Gemini C18 column and a water with 0.1% triethylamine/acetonitrile gradient) to afford 2-(6-fluoro-pyridin-3-yl)-9H-dipyrido[2,3-b;3',4'-d]pyrrole as off-white solid (14 mg, 88%).

MS: m/z=265.1 $(M+H)^+$.

Example 2

$^3$H-2-(6-Fluoro-pyridin-3-yl)-9H-dipyrido[2,3-b;3',4'-d]pyrrole

In a 2 ml tritiation flask, 2-(6-fluoro-pyridin-3-yl)-9H-dipyrido[2,3-b;3',4'-d]pyrrole (2.0 mg, 7.6 µmol; example 1) and Crabtree's catalyst (9.14 mg, 11.4 µmol) were dissolved in dichloromethane (0.8 mL) and DMF (0.2 mL). The flask was attached to the tritium manifold (RC-TRITEC) and degassed by freeze-pump-thaw. Tritium gas was introduced, and the light orange solution was vigorously stirred for 4 hours in an atmosphere of tritium at 450 mbar. The solution was cooled by liquid nitrogen and the excess tritium gas in the reaction vessel was reabsorbed on a uranium-trap for waste-tritium. The solvent was lyophilized off and labile tritium was removed by lyophilization with a 9:1-mixture of ethanol and water (3×1 mL) and toluene (2×1 mL). The remaining brownish oil was dissolved in ethanol (1.5 mL) and transferred on a SCX-2 cation exchanger. Remaining catalyst was eluted with MeOH (10 mL) and discarded, and the product was eluted with $NH_3$ in MeOH (3.5 N, 10 mL), collected separately and concentrated under reduced pressure. The crude product was purified by preparative HPLC (XBridge™ Prep, 5 µm, 10×250 mm) using acetonitrile, water, and pH 7 buffer as eluent. 37 MBq (1 mCi) of the title compound were obtained with a radiochemical purity of 99% and a specific activity of 936 GBq/mmol (25.3 Ci/mmol), determined by MS spectrometry. The compound was stored as a pH 7 buffer/DMSO solution.

MS: m/z=265.1 $[M+H]^+$, 267.1 $[M(^3H_1)+H]^-$, 269.1 $[M(^3H_2)+H]^+$

Example 3

[18F]-2-(6-Fluoro-pyridin-3-yl)-9H-dipyrido[2,3-b;3',4'-d]pyrrole a) 2-(6-Nitro-pyridin-3-yl)-9H-dipyrido[2,3-b;3',4'-d]pyrrole In a 50 mL flask (evaporated and purged with Ar), 2-chloro-dipyrido[2,3-b;3',4'-d]pyrrole-9-carboxylic acid tert-butyl ester (285 mg, 938 µmol), 2-nitropyridine-5-boronic acid pinacol ester (469 mg, 1.88 mmol), 1,1'-bis(diphenylphosphino)ferrocene-palladium(II)dichloride dichloromethane complex (34.5 mg, 42.2 µmol) and $K_2CO_3$ (389 mg, 2.81 mmol) were combined. DMF (24 mL) was added and the tube was sealed, evaporated and purged with Ar. The reaction mixture was heated to 90° C. and stirred for 18 h. Filtration through Celite® and subsequently through small silica gel pad (neutral, 60A, mesh 32-63) was followed by rinsing with sufficient DMF and evaporation to dryness. The brown solid is dissolved in DMF (20 mL) and DMSO was added until an almost clear solution resulted. After filtration, the solvents are evaporated to almost dryness. Purification by prep-HPLC provided the title compound (37 mg, 13%) as a yellow solid. MS m/z: 292.2 $[M+H]+$ b) [18F]-2-(6-Fluoro-pyridin-3-yl)-9H-dipyrido[2,3-b;3',4'-d]pyrrole The precursor, (0.7±0.3 mg) was dissolved in 400 μL it dimethylsulfoxide and sonicated prior to end of bombardment (EOB). At EOB, the aqueous [18F]fluoride ion, produced by proton bombardment of [18O]-enriched water, was trapped on an ion exchange column. The ion exchange column was eluted with 150 μL of a stock solution of Kryptofix 2.2.2®/potassium carbonate (48 mg of Kryptofix 2.2.2® and 10 mg potassium carbonate dissolved in 600 μL of 1:1 acetonitrile:water) into the reaction vial followed by 250 μL acetonitrile. The fluoride solution was evaporated to dryness at 110° C. via nitrogen flow and further dried azeotropically by two additions of acetonitrile (250 μL each). The reaction vial was remotely transferred to the microwave cavity (Resonance Instruments) and cooled with compressed air for 2 minutes. The precursor was added and then microwaved at 50 watts for 240 seconds after which the solution was quenched with 1 mL of water.

The reaction solution was diluted 3 mL triethylamine (TEA) buffer (pH 7.2) then injected onto the semi-preparative HPLC column (XBridge™ C18, 10 μm, 10×150 mm) eluted with 15:85 methanol:TEA buffer (pH 7.2) at 15 mL/min.

The HPLC effluent was monitored at 254 nm and an in-line radioactivity detector. The semipreparative chromatogram was observed and the [18F]-product peak was collected in 50 mL of water and reformulated using an automated SPE module. The product solution was eluted through a Waters C-18 SepPak Plus, washed with 10 mL of Milli-Q water, then eluted with 1 mL of absolute ethanol followed by 10 mL of normal saline into the final product vial via a 0.22 μm Millipore FG sterilizing filter.

Aliquots were removed from the final bottle for quality control analysis. Analytical HPLC (XBridge™ C18, 3.5 μm, 4.6×100 mm) elute with 40:60 methanol:TEA buffer (pH 7.2) at 2 mL/min monitored at 350 nm was performed to determine radiochemical and chemical purity, specific activity and chemical identity.

The 57-minute radio-synthesis of [18F]-2-(6-fluoro-pyridin-3-yl)-9H-dipyrido[2,3-b;3',4'-d]pyrrole produced an average final product of 330.5 mCi, 26.1% (n=2) non-decay corrected yield. The final product had an average specific radioactivity of 24,684 mCi/μmole and radiochemical purity of 99%.

The invention claimed is:

1. A compound of Formula I

Formula I wherein
R is hydrogen or tritium;
F is fluoro or $^{18}$fluoro;
or a pharmaceutically acceptable acid addition salt thereof.

2. The compound of Formula I according to claim 1, selected from the group consisting of
2-(6-fluoro-pyridin-3-yl)-9H-dipyrido[2,3-b;3',4'-d]pyrrole,
$^3$H-2-(6-fluoro-pyridin-3-yl)-9H-dipyrido[2,3-b;3',4'-d]pyrrole and
and [18F]-2-(6-fluoro-pyridin-3-yl)-9H-dipyrido[2,3-b;3',4'-d]pyrrole.
or a pharmaceutically acceptable acid addition salt thereof.

3. A process for the manufacture of a compound of Formula I as defined in claim 1 or a pharmaceutically acceptable acid addition salt thereof, comprising one of the following three methods, a)-c):

a) coupling a compound of Formula 2 (X=Cl, Br)

Formula 2 with a boronic acid or boronic acid ester of Formula 3

Formula 3 wherein R' is hydrogen or lower alkyl,
thus producing the following compound of Formula I, called Compound A Compound A wherein R is hydrogen,
and, optionally, converting Compound A into a pharmaceutically acceptable acid addition salt or into a compound of Formula I, wherein R is tritium by bombarding Compound A with tritium gas in the presence of a catalyst selected from iridium, ruthenium, rhodium and palladium containing complexes, in a solvent selected from dichloromethane, chlorobenzene, DMF and DMSO or mixtures thereof;
or b) coupling a compound of Formula 4

Formula 4

(X = Br, Cl, NO$_2$)

with a fluorinating reagent selected from potassium fluoride and tetrabutylammonium fluoride, thus producing Compound A of Formula I

Compound A wherein R is hydrogen,
and, optionally, converting Compound A into a pharmaceutically acceptable acid addition salt or into a compound of Formula I, wherein R is tritium by bombarding Compound A with tritium gas in the presence of a catalyst selected from iridium, ruthenium, rhodium and palladium containing complexes, in a solvent selected from dichloromethane, chlorobenzene, DMF and DMSO or mixtures thereof;
or
c) reacting a compound of Formula I Formula I wherein R is hydrogen, with tritium gas in the presence of a catalyst selected from iridium, ruthenium, rhodium and palladium containing complexes, in a solvent selected from dichloromethane, chlorobenzene, DMF and DMSO or mixtures thereof, thus producing the following compound of Formula I, called Compound B Compound B wherein R is tritium, and, optionally, converting Compound B into a pharmaceutically acceptable acid addition salt.

4. A pharmaceutical preparation comprising a compound of Formula I according to claim 1 or a pharmaceutically acceptable acid addition salt thereof, and a pharmaceutical acceptable carrier.

5. A method of diagnostic imaging tau-aggregate deposits, beta-amyloid aggregate deposits, or alpha-synuclein aggregate deposits, comprising
introducing into a mammal a detectable quantity of the preparation according to claim 4;
and
detecting the compound bound to one or more deposits selected from tau-aggregate deposits, beta-amyloid aggregate deposits, or alpha-synuclein aggregate deposits via diagnostic imaging.

6. The method of claim 5, wherein the deposits are tau-aggregate deposits.

* * * * *